United States Patent
Gonzalez et al.

[11] Patent Number: 6,007,534
[45] Date of Patent: Dec. 28, 1999

[54] BONE STABILIZING APPARATUS

[76] Inventors: Onofre Gonzalez; Hector Daniel Colletta, both of Castro Barros 92, Bernal, Provincia de Buenos Aires, Argentina

[21] Appl. No.: 09/036,190

[22] Filed: Mar. 6, 1998

[51] Int. Cl.[6] ................................................ A61B 17/56
[52] U.S. Cl. .................................................. 606/54; 606/59
[58] Field of Search ................................ 606/54, 55, 57, 606/58, 59

[56] References Cited

U.S. PATENT DOCUMENTS

| | | | |
|---|---|---|---|
| 4,312,336 | 1/1982 | Danieletto et al. | 606/57 |
| 4,621,627 | 11/1986 | DeBastiani et al. | 606/54 |
| 4,848,368 | 7/1989 | Kronner | 606/57 |
| 5,160,335 | 11/1992 | Wagenknecht | 606/57 |
| 5,207,676 | 5/1993 | Canadell et al. | 606/54 |
| 5,320,622 | 6/1994 | Faccioli et al. | 606/58 |
| 5,454,810 | 10/1995 | Pohl et al. | 606/54 |

*Primary Examiner*—Michael Buiz
*Assistant Examiner*—Daphna Shai
*Attorney, Agent, or Firm*—William B. Ritchie; Michael J. Persson

[57] ABSTRACT

A bone stabilization apparatus that helps to minimize torsion effects of the attachment nails or screws which have been placed in the bone. The apparatus has two ends for attachment to a bone and has an axis where the device includes a first bar member having a clamp end and a nozzle end, a second bar member having a clamp end and nozzle end, and a distancing bar having a first end, a second end, and an anti-rotation groove where the ends of the distancing bar are attached. The length of the apparatus is selectively adjustable, and the clamps and longitudinal axis of the central body can be set independent of the axis of the bone.

5 Claims, 2 Drawing Sheets

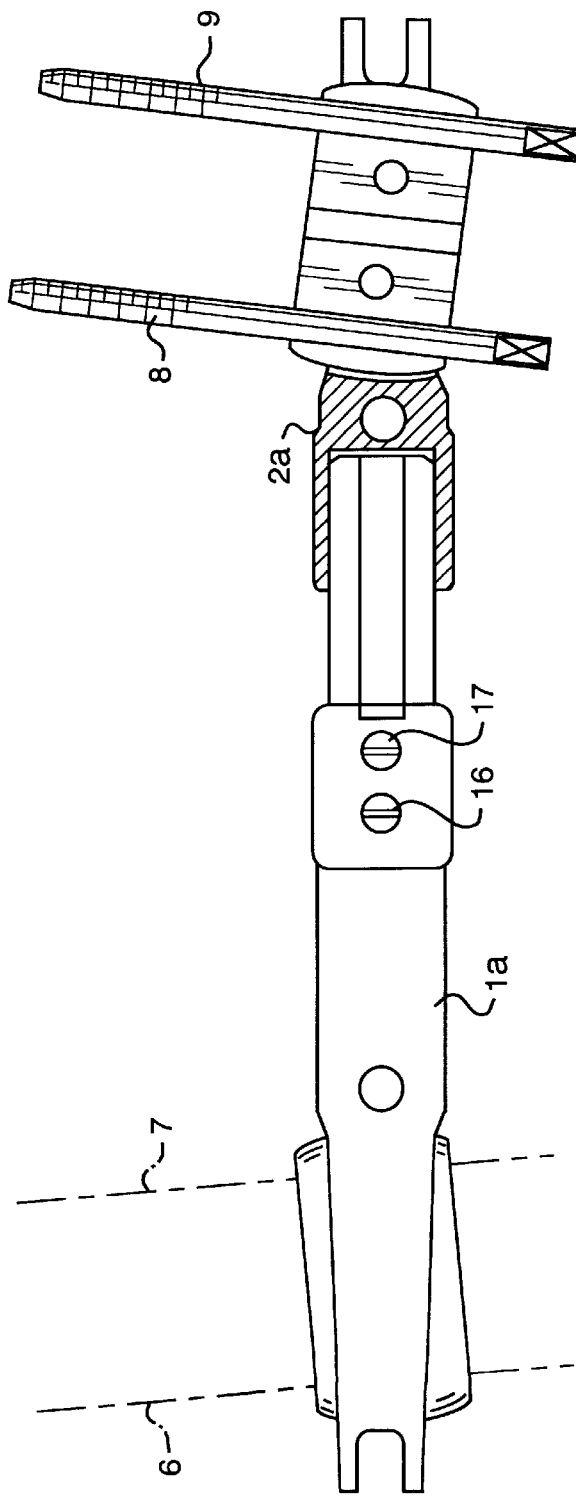
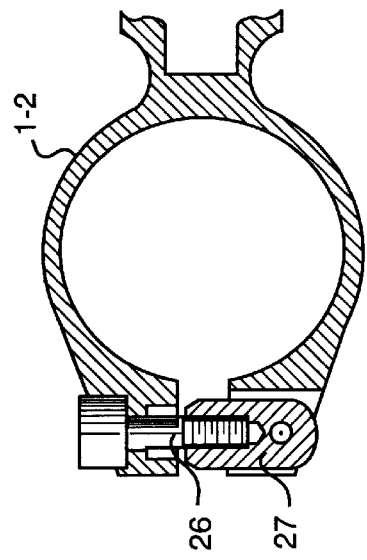
FIG. 1
FIG. 3

BONE STABILIZING APPARATUS

The present invention takes into account and has an objective as an external device for osseous stabilization. The invention can also be used as a bone elongation or compressor or as a modifier of angles or outlets of bone axis, bearing traumatic or constitutional characteristics.

Prior art devices are generally made up of a bar or variable length, bearing nail or screw holder elements on each side, that are mounted with a universal movement. Everything as well, with the variances that are to be supposed, thus referring to the media used in order to fix the position to these nails, also tending to control the universal movement of their respective supporting elements.

It happens sometimes, that they are very complex devices, that do not grant a high safety coefficient regarding the fixing of the nail holder elements, neither bearing the possibility of a shorter minimum distance between the nails.

Comparing and seen as an advantage, the invention conveys to their nails or screws, placed between the integrative parts rotula clamps, respectively adjusted inside the pertinent clamp heads, which make up the device and are connected by means of a distance rod, on which at least one of the same can be displaced, in order to be fixed at the spacing position, that corresponds respect to the other element.

With the device organized this way, the following benefits are achieved:

1) The fixing of the nails or screws to the pertinent rotula clamps makes the angular position of the same independent of the position that could be necessarily required by the system of longitudinal stabilization.
2) The minimization of the torsion efforts sent by said nails or screws to the bone structure of the patient and in this case, due to the high efficiency of the fixing of the rotula clamp by means of another clamp (made up by the clamp head) that surrounds it externally.
3) An increase of the safety coefficient at the fixing of the rotula clamp and consequently at the bone stabilization, due precisely to the great diameter of said rotula clamp and to the great value of the friction coefficient, that is set up between said rotula clamp and the inner surface of the corresponding clamp head.
4) The control over the movement of each rotula clamp by means of only one fixing screw, which redounds in the benefit of a consequent simplification at the stabilization process.
5) A shorter minimum distance between contiguous nails or screws that, in this case, is provided by the fact that the carrying element of the same is the rotula clamp.
6) An absolutely free space between the nail or screw holder elements that allows to reach by means of the provision of the proper distance bar any of the positions related to distances.
7) A smaller amount of integrating parts of the device that tend to a constructive and functional simplification.
8) The possibility of incorporating an auxiliary device of controlled elongation, and in this case, the supply of two proper supports.

Because of its constructive peculiarities and in order to anticipate the real scope of this invention, it could be stated, that the created device is characterized because of comprising two clamp heads with fixing screws, invested with two nozzles of which at least one is mounted on a groove and fixed on a distance bar that is a projection of the other. Said nozzles are invested with supporting pieces of an auxiliary device for controlled elongation, thus being adjusted in the pertinent rotula clamps that carry sets of nails or screws of osseous application.

With the purpose that the present invention could be improved and better understood, the same will be hereinafter described in detail, thus referring to the example of practical performance that has been represented at the annexed illustrations.

BRIEF DESCRIPTION OF THE DRAWINGS

FIG. 1 is a longitudinal view in plant and in partial sectional view of the invented device.

FIG. 3 is the detail of a variance of the performance.

At said figures, the same reference signs indicate equal or corresponding parts.

DETAILED DESCRIPTION OF THE INVENTION

Figure 2:
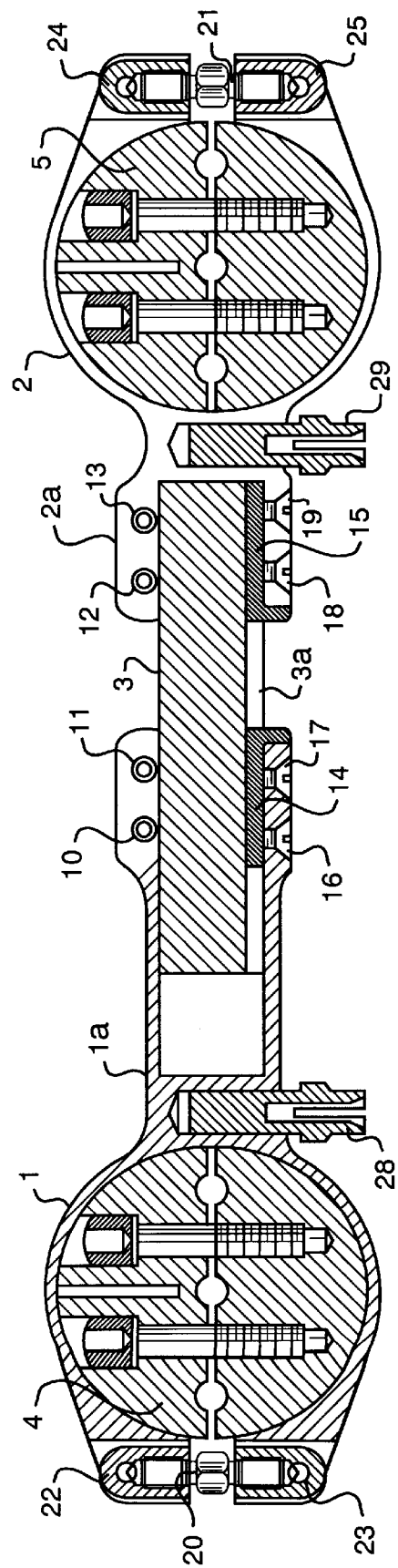
FIG. 2 is a horizontal longitudinal view of the same device.

According to FIGS. 1 and 2, the external device of stabilization that makes up the real object of the present invention and comprises the pair of clamp heads 1 and 2, the distance bar 3 on which they are mounted and the pair of rotula clamps 4 and 5, which constitute the support of the respective sets of parallel nails or screws 6-7 and 8-9, applicable to the bones of the patient, are supplied as a unit, thus being adjusted to each one of said clamp heads 1 and 2.

It should be stated that the number of nails or screws at each of both sets could be greater, but always placed as a unit between the corresponding grooves that are performed at the integrating parts of each rotula clamp and inclusive as a selective form in order to obtain all possible variations concerning the relative distance of said nails or screws.

The clamp heads 1 and 2 have their respective mounting nozzles 1a and 2a that are longitudinally separated on the long side of one of its generatrixes, thus being invested with the corresponding pairs of fixing screws 10-11 and 12-13; inclusive, said nozzles are respectively supplied with the bolts or contact pins 14 and 15, duly adjusted in each case by means of the screw pairs 16-17 and 18-19, being the first made up of a groove related to a longitudinal slot 3a belonging to the distance bar 3, and the second one of an anti-rotate part for the same bar.

This way, and this taking into account that the distance bar 3 tends to be a stem or rod that belongs to the clamp head 2, the other clamp head 1 can be moved towards the relative position that might be necessary in order to procure the desired longitudinal stabilization. Nevertheless and even though it has not been illustrated, there are no hindrances for both clamp heads 1 and 2 to be movable and for said distance bar 3 to be an integral stem or rod of one of the same.

Said clamp heads 1 and 2 are closed by a screw and respectively by the screws indicated at the references 20 and 21 at FIG. 1 that are twisted at their ends at the pertinent pairs of nuts 22, 23, 24 and 25, thus being joint as a unit at the corresponding opposing ends of each clamp head.

To these respects, nevertheless, there exists an alternative concerning performance described at FIG. 3 where as a more simple and practical option, a kind of "Allen" screw 26 is hereby used that screws in through the only articulated screw 27 at the other end by means of one of the ends of the clamp head 1 or 2.

In both cases, as it could possibly be inferred, the fact that the hereinbefore described nuts are articulated, means that it is impossible to alter the disposition of the closing media whenever the device is handled.

As a complement and at the mounting nozzles 1.*a* an 2.*a*, the device is respectively invested with the supports or brackets 28 and 29 for an auxiliary device of controlled elongation, thus being conventional and therefore, not represented at these present.

What is claimed is:

1. A bone stabilizing apparatus and having two ends for attachment to a bone having an axis, said apparatus comprising:

a first bar member having a clamp end and a nozzle end;

a second bar member having a clamp end and a nozzle end;

a distancing bar having a first end, a second end, and an anti-rotation groove longitudinally position thereon, such that the first end of said distancing bar is inserted into the nozzle end of said first bar member and is adjustably affixed thereto; and such that the second end of said distancing bar is inserted into the nozzle end of said second bar member and is adjustably affixed thereto, wherein at least one of said bar members is affixed to said distancing bar utilizing the anti-rotation groove of said distancing bar and wherein the total length of said apparatus is selectively adjustable and defines an axis of longitudinal stabilization;

a first rotula clamp having at least one point of attachment for a nail or a screw which serves to anchor one end of said apparatus to the bone via the point of attachment, wherein said rotula clamp is inserted into the clamp end of said first bar member and is adjustably affixed therein;

a second rotula clamp having at least one point of attachment for a nail or a screw which serves to anchor the other end of said apparatus to the bone via the point of attachment, wherein said rotula clamp is inserted into the clamp end of said second bar member and is adjustably affixed therein; wherein the point of attachment of said first rotula clamp and the point of attachment of said second rotula clamp occupy the same relative positioning in their respective said rotula clamps; and wherein each of said rotula clamps may be selectively independently angled to the longitudinal axis of said apparatus, so that the angles of the rotula clamps and axis of longitudinal stabilization relative to the axis of the bone are selectively independent to one another.

2. The apparatus of claim 1 at least one of said bar members is integral with said distancing bar.

3. The apparatus of claim 1 where each of said bar members has a length and each length of said bar members is different from one another.

4. The apparatus of claim 1 wherein the clamp end of each of said bar members further comprises two semicircular arms that are open at the ends, with the open end of said semicircular arms each having a threaded recess wherein a single threaded screw inserted therethrough into said threaded recesses of said semicircular arms causes said semicircular arms to move toward one another thus holding the respective rotula inserted therein firmly in position.

5. The apparatus of claim 1 wherein each of said bar members further comprises at attachment support for attaching an auxiliary device for controlling elongation.

* * * * *